(12) United States Patent
Nishimura et al.

(10) Patent No.: US 9,657,262 B2
(45) Date of Patent: *May 23, 2017

(54) FERMENTATION APPARATUS THAT USES BIOMASS AS FEEDSTOCK

(75) Inventors: Akira Nishimura, Hyogo (JP); Takahiro Yamauchi, Hyogo (JP); Kentaro Ogura, Hyogo (JP); Haruka Nishimoto, Hyogo (JP); Hiroyuki Kurihara, Kanagawa (JP); Atsushi Minamino, Kanagawa (JP); Hideo Suzuki, Tokyo (JP); Gaku Kondo, Tokyo (JP)

(73) Assignee: TORAY INDUSTRIES, INC., Tokyo (JP)

(*) Notice: Subject to any disclaimer, the term of this patent is extended or adjusted under 35 U.S.C. 154(b) by 223 days.

This patent is subject to a terminal disclaimer.

(21) Appl. No.: 13/982,645

(22) PCT Filed: Mar. 23, 2012

(86) PCT No.: PCT/JP2012/057566
§ 371 (c)(1),
(2), (4) Date: Jul. 30, 2013

(87) PCT Pub. No.: WO2012/128358
PCT Pub. Date: Sep. 27, 2012

(65) Prior Publication Data
US 2013/0337552 A1    Dec. 19, 2013

(30) Foreign Application Priority Data
Mar. 24, 2011   (JP) ................................ 2011-066768

(51) Int. Cl.
*C12M 1/00* (2006.01)
*C13B 20/16* (2011.01)
(Continued)

(52) U.S. Cl.
CPC ............ *C12M 29/04* (2013.01); *C12M 21/12* (2013.01); *C12M 45/02* (2013.01); *C12M 45/03* (2013.01);
(Continued)

(58) Field of Classification Search
CPC ...... C12M 21/12; C12M 29/04; C12M 45/02; C12M 45/03; C12M 45/04; C12M 45/09;
(Continued)

(56) References Cited

U.S. PATENT DOCUMENTS 6,406,546 B1   6/2002 Donovan et al.
2007/0259412 A1   11/2007 Belanger et al.
(Continued)

FOREIGN PATENT DOCUMENTS

EP   2 251 427 A1   11/2010
JP   09-507386 A    7/1997
(Continued)

OTHER PUBLICATIONS

WO2010067785 Kurihara corresponding description from EP2371973 (2010).*
(Continued)

*Primary Examiner* — Gautam Prakash
(74) *Attorney, Agent, or Firm* — Westerman, Hattori, Daniels & Adrian, LLP

(57) ABSTRACT

An apparatus for treating a biomass feedstock at a high temperature, includes a cooling device 90 for cooling a biomass treated liquid at a high temperature; an enzymatic saccharification tank 103 for saccharifying a cooled treated liquid 101B with an enzyme; a solid-liquid separation apparatus 112 for removing water-slightly soluble substances contained in a saccharide solution 104 taken out from the enzymatic saccharification tank 103 and a foreign substance removing unit 113 provided with a microfiltration (MF) membrane 113a; a dilution tank 132, disposed downstream of the foreign substance removing unit 113, for diluting the saccharide solution from which the water-slightly soluble substances are removed by adding water thereto; a water separation unit 116, provided with a reverse osmosis (RO)
(Continued)

membrane 116a, for removing water 114 from the diluted saccharide solution so as to obtain concentrated saccharide solution 115.

2 Claims, 6 Drawing Sheets

(51) Int. Cl.
```
C13K 1/04      (2006.01)
C12M 1/33      (2006.01)
C12P 19/02     (2006.01)
C12P 19/14     (2006.01)
C12P 7/10      (2006.01)
```

(52) U.S. Cl.
CPC ............ *C12M 45/04* (2013.01); *C12M 45/09* (2013.01); *C12M 45/20* (2013.01); *C12P 7/10* (2013.01); *C12P 19/02* (2013.01); *C12P 19/14* (2013.01); *C13B 20/165* (2013.01); *C13K 1/04* (2013.01); *C12P 2201/00* (2013.01); *Y02E 50/16* (2013.01)

(58) Field of Classification Search
CPC ......... C12M 45/20; C12P 19/02; C12P 19/14; C12P 2201/00; C12P 7/10; C13B 20/165; C13K 1/04; Y02E 50/16
USPC ...................................................... 435/288.7
See application file for complete search history.

(56) References Cited

U.S. PATENT DOCUMENTS

| | | | |
|---|---|---|---|
| 2008/0032344 | A1 | 2/2008 | Fallavollita |
| 2010/0184176 | A1 | 7/2010 | Ishida et al. |
| 2010/0285574 | A1 | 11/2010 | Genta et al. |
| 2011/0003348 | A1 | 1/2011 | Genta et al. |
| 2011/0008826 | A1 | 1/2011 | Hanakawa et al. |
| 2011/0250637 | A1 | 10/2011 | Kurihara et al. |

FOREIGN PATENT DOCUMENTS

| | | | |
|---|---|---|---|
| JP | 11-506394 A | 6/1999 | |
| JP | 11-506934 A | 6/1999 | |
| JP | 2005-168335 A | 6/2005 | |
| JP | 2007/129921 A1 | 11/2007 | |
| JP | 2009-183153 A | 8/2009 | |
| JP | 2009-183154 A | 8/2009 | |
| JP | 2009-183805 A | 8/2009 | |
| JP | 4436429 B1 | 3/2010 | |
| JP | 2011-205987 A | 10/2011 | |
| JP | 2011-223975 A | 11/2011 | |
| WO | 95-17517 A1 | 6/1995 | |
| WO | 96/40970 A1 | 12/1996 | |
| WO | 96-40970 A1 | 12/1996 | |
| WO | 2008/017145 A1 | 2/2008 | |
| WO | 2009/110374 A1 | 9/2009 | |
| WO | 2010/067785 A1 | 6/2010 | |
| WO | 2011/111451 A1 | 9/2011 | |

OTHER PUBLICATIONS

JP 2009-183805 Genda English translation (2009).*
S. Kumagai et al., "Fractionation and Saccharification of Cellulose and Hemicellulose in Rice Hull by Hot-Compressed-Water Treatment with Two-Step Heating", J. Jpn. Inst. Energy., 2004, vol. 83, No. 10, pp. 776-781.
Y. Nagashima et al., "Comparison of Hydrothermal Decomposition of Biomass between Batch and Semi-batch Treatment", The Japan Institute of EnergyTaikai Koen Yoshishu, 2010, vol. 19th, pp. 186-187.
S. Kumagai et al., "Characteristics of Hydrothermal Decomposition and Saccharification of Various Lignocellulosic Biomass and Enzymatic Saccharification of the Obtained Hydrothermal-Residue" J. Jpn. Inst. Energy., 2007, vol. 86, No. 9, pp. 712-717.
S. Kumagai et al., "Characteristics of decomposition and saccharification of various lignocellulosic biomass under hydrothermal conditions", Biomass Kagaku kaigi Happyo Ronbunshu, 2007, vol. 2nd, pp. 34-35.
T. Persson et al., "Isolation of hemicelluloses by ultrafiltration of thermomechanical pulp mill process water-Influence of operating conditions", Chem. Eng. Res. Des., 2010, vol. 88, pp. 1548-1554.
International Search Report for PCT/JP2012/057567, Mailing date of May 1, 2012.
Written Opinion for PCT/JP2012/057567, Mailing Date of May 1, 2012, with English translation.
Office Action dated Jan. 6, 2015, issued in corresponding Japanese Patent Application No. 2011-066768, with English translation (10 pages).
Nomura, Kazuhiro et al., "Biomass Ethanol", Nikkei Biotechnology & Business, Japan, 2002, pp. 52-61, w/ partial English translation.
Written Opinion dated May 17, 2012, issued in coppresponding application No. PCT/JP2012/057566.
International Search Report dated Jun. 12, 2012, issued in corresponding application No. PCT/JP2012/057566.
Australian Office Action dated Nov. 4, 2014, issued in Australian Patent Application No. 2012232937 (3 pages).
English Translation of the Written Opinion of PCT/JP2012/057566 mailing date of Jun. 12, 2012.
Nagashima, Yoshinou et al., "Comparison of Hydrothermal Decomposition of Biomass between Batch and Semi-batch Treatment," the 19th annual Meeting of Japan Institute of Energy, Jan. 29, 2015 pp. 186-187.
Kumagai, Satoshi et al., "Fractionation and Saccharification of Cellulose and Hemicellulose in Rice Hull by Hot-Compressed-Water Treatment with Two-Step Heating," Journal of the Japan Institute of Energy, vol. 83, No. 10, Jan. 29, 2015, pp. 776-781.
Office Action dated Jan. 27, 2015, issued in corresponding Japanese Patent Application No. 2011-066769, w/ English translation. (9 pages).
Final Office Action dated Aug. 14, 2015, issued in U.S. Appl. No. 13/982,420 (21 pages).
Notice of Acceptance dated Aug. 13, 2015, issued in Australian Patent Application No. 2012232938 (counterpart of U.S. Appl. No. 143/982,420) (3 pages).
Notice of Acceptance dated Apr. 15, 2015, issued in Australian Patent Application No. 2012232937 (42 pages).
Notice of Allowance dated Apr. 27, 2015, issued in Canadian Patent Application No. 2825542 (corresponds to U.S. Appl. No. 13/982,420) (2 pages).
Office Action dated May 4, 2015, issued in U.S. Appl. No. 13/982,420 (33 pages).
Notice of Acceptance dated Apr. 15, 2015, issued in Australian Patent Application No. 2012232937 (corresponds to U.S. Appl. No. 13/982,420) (42 pages).
Notice of Allowance dated Apr. 27, 2015, issued in Canadian Patent Application No. 2825542 (2 pages).

* cited by examiner

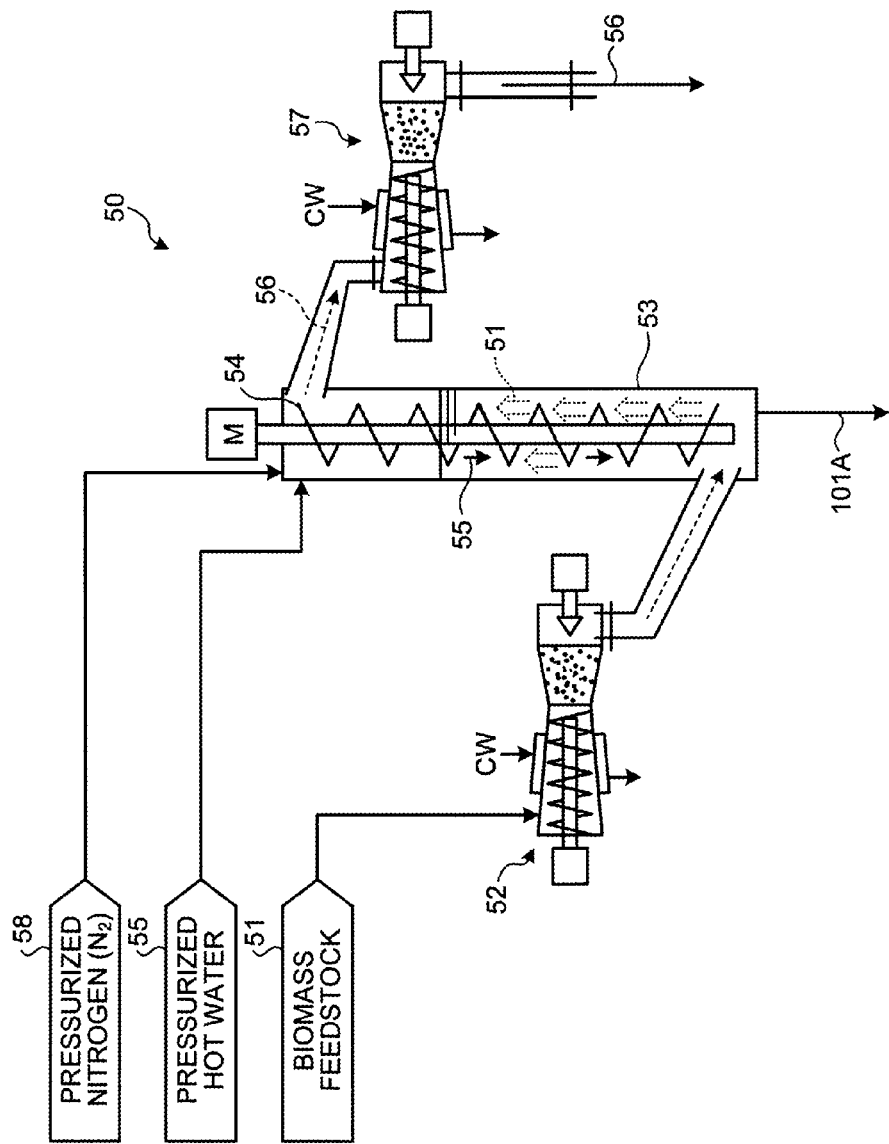

US 9,657,262 B2

FERMENTATION APPARATUS THAT USES BIOMASS AS FEEDSTOCK

FIELD

The present invention relates to a fermentation apparatus that uses biomass as a feedstock.

BACKGROUND

Production technology of ethanol or the like has hitherto been practically used in which after saccharification treatment of biomass such as wood with dilute sulfuric acid or concentrated sulfuric acid, solid-liquid separation is performed, and an aqueous phase is neutralized, which is utilized as a feedstock for ethanol fermentation (Patent Literature 1, and Patent Literature 2).

Chemical industry feedstock production (for example, lactic acid fermentation, and the like) using saccharide as a starting feedstock can also be considered.

Here, biomass refers to an accumulation of organisms or organic substances derived from an organism, which is incorporated in a material cycle in the global biosphere (see JIS K 3600 1258).

Here, sugarcanes, corns, and the like, which are now used as the feedstock for an alcohol, are originally provided for food, and thus it is not preferable that these edible resources are stably employed for industry for long term in terms of the life cycle of available foodstuffs.

Thus, effective utilization of cellulose resources such as herbaceous biomass or woody biomass, which are expected to be useful resources in the future, is an important issue.

In addition, the cellulose resource include variously such as 38 to 50% cellulose, a 23 to 32% hemicellulose component, and a 15 to 22% lignin component, which is not a fermentation feedstock, which are each different. Because of industrialization research with many problems, only fixed feedstock is considered, and production system technology considering versatility of feedstock has not yet been disclosed in the present circumstances.

In addition, the production system in which the fixed feedstock is considered has little point, because it is, originally, considered for the purpose of measurements of garbage problem or prevention of global warming in a manner disadvantageous to the fermentation feedstock, compared to a starch feedstock. General waste must be widely applicable. Enzymatic saccharification method itself has also excessive low efficiency, which is a prospective issue in the present circumstances. A saccharification ratio with an acid treatment is considerably small value such as about 75% (based on a component capable of saccharification), because of overdecomposition of saccharide caused by an excessive reaction. A production ratio of ethanol is, accordingly, up to about 25% to a cellulose resource (Non Patent Literature 1 and Patent Literature 3).

Additionally, according to the conventional techniques of Patent Literatures 1 to 3, by-products cause enzymatic saccharification inhibition, thereby occurring a phenomenon in which a saccharide yield is reduced, and thus hydrothermal decomposition apparatuses, by which enzymatic inhibitory substances are removed to increase saccharification activity of enzyme by mainly cellulose, have been previously proposed (Patent Literatures 4 and 5).

CITATION LIST

Patent Literature

Patent Literature 1: Japanese National Publication of International Patent Application No. 9-507386
Patent Literature 2: Japanese National Publication of International Patent Application No. 11-506934
Patent Literature 3: Japanese Laid-open Patent Publication No. 2005-168335
Patent Literature 4: Japanese Laid-open Patent Publication No. 2009-183805
Patent Literature 5: Japanese Laid-open Patent Publication No. 2009-183154

Non Patent Literature

Non Patent Literature 1: Nikkei Biotechnology Business, p 52, September 2002

SUMMARY

Technical Problem

According to the proposal of the hydrothermal decomposition apparatus in Patent Literatures 4 and 5 described above, biomass and pressurized hot water are supplied while they are brought into countercurrent contact to each other, to perform hydrothermal reaction due to internal heat exchange, but the internal temperature is a high temperature of 180 to 240° C., and a pressure 0.1 to 0.4 MPa higher than the saturated vapor pressure of water at that temperature is applied to perform the decomposition treatment, thus resulting in containing with decomposition products of lignin and the like in the biomass treated liquid at a high temperature (pressurized hot water effluent) after the reaction.

It has been revealed that with respect to a pressurized hot water soluble component dissolved in this biomass treated liquid at a high temperature, a part of the pressurized hot water soluble component, which has been once dissolved in pressurized hot water, is precipitated, and is solidified or is formed into a colloidal water-slightly soluble substance, because the reaction mixture is cooled to an enzymatic saccharification temperature (for example, 60° C. or lower), in a saccharification step of a subsequent step. It has been further found in the present invention that this water-slightly soluble substance has an inhibitory function of growth of microorganisms and fermentation production in the fermentation step of the subsequent step.

Thus, the present invention provides a fermentation apparatus that uses biomass as a feedstock, which includes an apparatus capable of efficiently removing water-slightly soluble substances, which are generated during decomposition of a biomass feedstock in conditions of a high temperature and a high pressure, after enzymatic saccharification, which are the problems described above.

Solution to Problem

According to a first aspect of the present invention, there is provided a fermentation apparatus that uses biomass as a feedstock including: a hydrothermal decomposition apparatus for performing a high temperature and high pressure treatment in a temperature range of 180° C. to 240° C., while bringing a biomass feedstock including at least cellulose, hemicellulose, and lignin into countercurrent contact with pressurized hot water; a cooling means for cooling biomass treated liquid at a high temperature which has been discharged from the apparatus; an enzymatic saccharification tank for saccharifying the cooled treated liquid with an enzyme; a solid-liquid separation apparatus for removing a water-slightly soluble fermentation inhibitory substance contained in the saccharide solution taken from the enzymatic saccharification tank; a foreign substance removing unit provided with a microfiltration (MF) membrane; a dilution tank disposed downstream of the foreign substance removing unit for adding water so as to dilute the saccharide solution from which the water-slightly soluble fermentation inhibitory substance has been removed; a water separation unit provided with a reverse osmosis (RO) membrane, for removing water from the diluted saccharide solution so as to obtain concentrated saccharide solution; and a fermentation tank for fermenting the concentrated saccharide solution.

According to a second aspect of the present invention, there is provided the apparatus according to the first aspect, including: a saccharide solution purification tank for retaining the saccharide solution taken out from the enzymatic saccharification tank; a solid-liquid separation unit disposed via a first circulation line from the saccharide solution purification tank, for removing a water-slightly soluble fermentation inhibitory substance from the taken saccharide solution; and a foreign substance removing unit disposed via a second circulation line from the saccharide solution purification tank, the foreign substance removing unit including a microfiltration (MF) membrane for removing a water-slightly soluble fermentation inhibitory substance from the taken saccharide solution.

According to a third aspect of the present invention, there is provided the apparatus according to the second aspect, in which the enzymatic saccharification tank and the saccharide solution purification tank are integrated.

According to a fourth aspect of the present invention, there is provided the apparatus according to the third aspect, including a dilution tank for adding water so as to dilute the saccharide solution which has been treated in the foreign substance removing unit to remove the water-slightly soluble substance therefrom; and a water separation unit including a reverse osmosis (RO) membrane for separating water from the diluted saccharide solution.

According to a fifth aspect of the present invention, there is provided the apparatus according to any one of the first to fourth aspects, including a first measurement unit for measuring either or both of a turbidity or/and an absorbance of the saccharide solution from which the water-slightly soluble fermentation inhibitory substance has been removed.

According to a sixth aspect of the present invention, there is provided the apparatus according to the fifth aspect, including a second measurement unit for measuring either or both of a turbidity and an absorbance of the saccharide solution after addition of yeast.

Advantageous Effects of Invention

According to the apparatus of the present invention, water-slightly soluble fermentation inhibitory substances, which are generated during a high temperature and high pressure treatment at 180° C. to 240° C. while a biomass feedstock including at least cellulose, hemicellulose and lignin is brought into countercurrent contact with pressurized hot water, is completely removed, whereby saccharide solution having less impurities can be obtained. As a result, it is also possible to concentrate the saccharide solution using reverse osmosis membrane in a subsequent stage, whereby the saccharide solution having a higher concentration than those in conventional methods can be produced. Fermentation inhibition can be suppressed with the improvement of the saccharide solution described above.

BRIEF DESCRIPTION OF DRAWINGS

FIG. 7 is a schematic view illustrating a hydrothermal decomposition apparatus of biomass according to Example 1.

DESCRIPTION OF EMBODIMENTS

Figure 1:
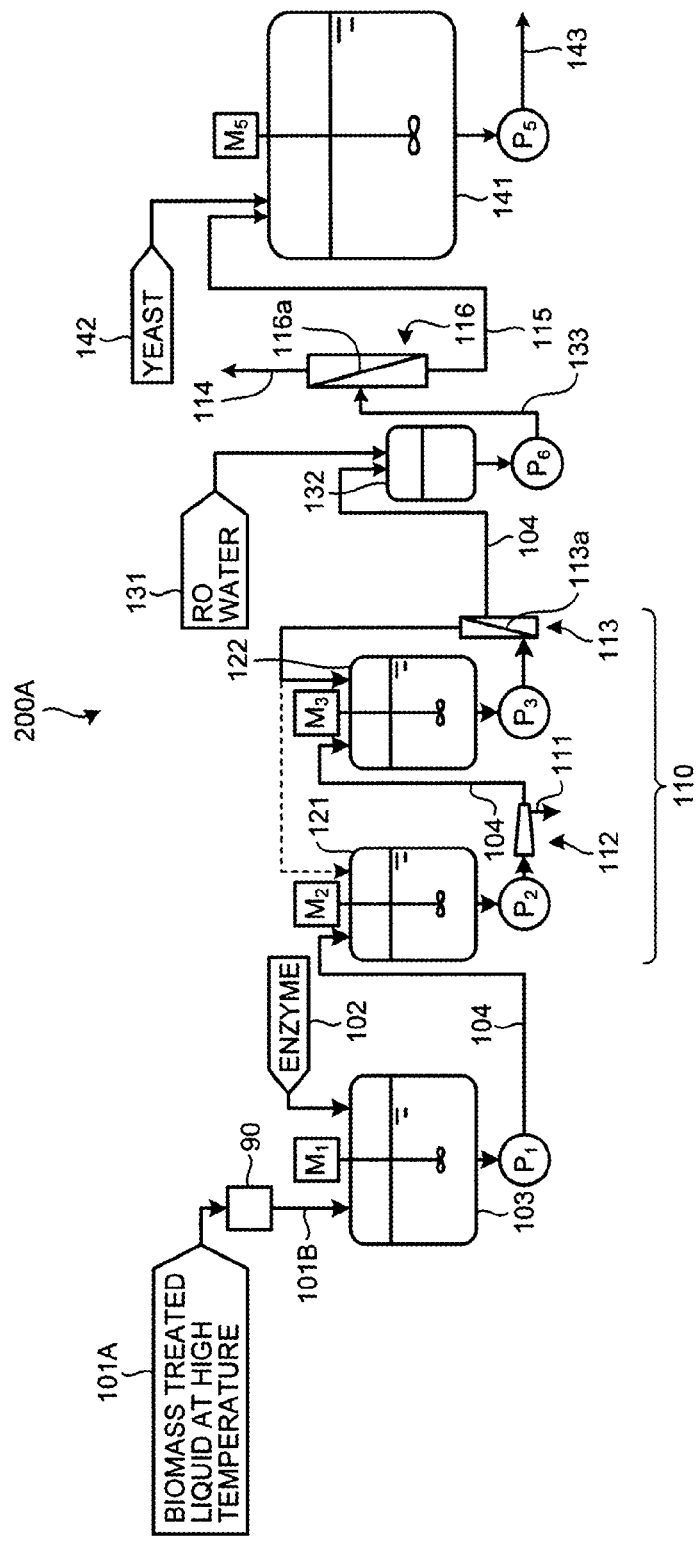
FIG. 1 is a schematic view of a fermentation apparatus that uses biomass as a feedstock according to Example 1.

The present invention will be explained in detail in reference to views below. The present invention is not limited to these Examples. In addition, constituent features described in Examples below include one which can be easily considered by those skilled in the art and ones which are substantially the same as those.

Example 1

The fermentation apparatus using a biomass feedstock according to the present invention will be explained in reference to views.

FIG. 7 is the schematic view illustrating a hydrothermal decomposition apparatus of biomass according to Example 1.

First, a "hydrothermal decomposition apparatus (50) in which a high temperature and high pressure treatment is performed at a temperature range of 180° C. to 240° C. while a biomass feedstock including at least cellulose, hemicellulose and lignin is brought into countercurrent contact with pressurized hot water" is explained using FIG. 7.

The hydrothermal decomposition apparatus 50 is a vertical type apparatus, as illustrated in FIG. 7, but the present invention is not limited thereto, and may be an inclined type or horizontal-type hydrothermal decomposition apparatus. As the hydrothermal decomposition apparatus, the inclined type and the vertical type are more preferable. This is because gases generated during hydrothermal decomposition reaction and gases carried in a feedstock can quickly escape from upper parts, which is preferable. In addition, because decomposition products are extracted with pressurized hot water 55, a concentration of extracts is increased from an upper side toward a bottom side, which is thus preferable in terms of extraction efficiency.

According to the hydrothermal decomposition apparatus 50 of the present Example, a conveying screw means 54 is provided; as a result, 1) a solid component can be conveyed by solid-liquid counter-flow, 2) solid-liquid separation can be performed in an apparatus body 53, and 3) mixing of pressurized hot water 55 on the surface and the inside of the solid is advanced in the apparatus body 53, whereby the reaction is promoted.

In the hydrothermal decomposition apparatus 50 according to the present Example, a biomass feedstock (for example, a straw, and the like in the present Example) 51 is supplied through a biomass supplying apparatus 52 at a normal pressure or under pressure; pressurized hot water 55 is supplied from an edge side different from the supplying side of the biomass feedstock 51 into the inside of the apparatus body 53; hydrothermal decomposition is performed while the biomass feedstock 11 is brought into countercurrent contact with the pressurized hot water 55 to transfer a lignin component and a hemicellulose into the pressurized hot water 55, thereby separating the lignin component and the hemicellulose component from the biomass feedstock 51; and a biomass solid component 56 is discharged through a biomass discharging apparatus 57 under pressure or at a normal pressure. In the view, reference sign 58 shows pressurized nitrogen.

Here, the biomass feedstock, which is supplied to the hydrothermal decomposition apparatus 50, is not particularly limited, and refers to an accumulation of organisms or organic substances derived from an organism incorporated in a material cycle in the global biosphere (see JIS K 3600 1258). In the present invention, it is particularly preferable to use cellulose resources such as wood including, for example hardwoods, and herbaceous plants, agricultural wastes, food wastes.

The particle size of the biomass feedstock is not particularly limited, and it is preferable to mill it to a size of, for example, five mm or less.

In the present Example, a pre-treatment using a mill as a pre-treatment apparatus may be performed before the biomass is supplied. Washing using a washing apparatus may also be performed.

When as the biomass feedstock was used for, for example, chaff, it can be supplied to the hydrothermal decomposition apparatus 50 as it is, without the mill treatment.

It is preferable to set a reaction temperature in the hydrothermal decomposition apparatus 50 at a range of 180° C. to 240° C., more preferably 200° C. to 230° C.

This is because a hydrothermal decomposition speed is slow at a low temperature of lower than 180° C., and thus a long retention time is required, leading to increasing in size of the apparatus, which is not preferable. On the other hand, when the temperature is higher than 240° C., the decomposition speed becomes excessive, which increases the transfer of the cellulose component from the solid to the liquid side and, at the same time, promotes the excessive decomposition of the hemicellulose saccharides, which is not preferable.

The hemicellulose component starts to dissolve at about 140° C., the cellulose starts to dissolve at about 230° C., and the lignin component starts at about 140° C. It is preferable to set a temperature to a range of 180° C. to 240° C., where the cellulose remains on the solid component side, and the hemicellulose component and the lignin component have sufficient decomposition speeds.

It is preferable to set a reaction pressure to a pressure about 0.1 to 0.5 MPa higher than a saturated vapor pressure of water having each temperature at which the pressurized hot water 55 exists inside the apparatus body 53.

The reaction time is preferably 20 minutes or less, or from three minutes to 10 minutes. This is because if the reaction is continued for a long time, a ratio of the excessively decomposed products is increased, which is not preferable.

In the hydrothermal decomposition apparatus 50, when the biomass feedstock 51 is brought into countercurrent contact with the pressurized hot water 55, it is preferable to make uniform pressurized hot water flow.

Biomass treated liquid at a high temperature 101A in the present invention can be obtained by using such a hydrothermal decomposition apparatus 50.

The pressurized hot water 55 may have any pH value of alkaline, neutral and acidic ranges. When it is alkaline, sodium hydroxide, hydrated lime, ammonia, and the like may be used, and when it is acidic, dilute sulfuric acid, hydrochloric acid, phosphoric acid, and the like may be used. When the pressurized hot water 55 is alkaline or acidic, it has an advantage in which the pre-treatment of the biomass can be efficiently advanced. On the other hand, however, it has disadvantages in which it is necessary to complete the pH adjustment before enzyme is thrown, and it is necessary to prepare chemicals for adjusting the pH and to provide a pH adjusting apparatus.

FIG. 1 is the schematic view of the fermentation apparatus that uses biomass as a feedstock according to Example 1.

Next, a fermentation apparatus 200A that uses biomass as a feedstock will be explained using FIG. 1, which includes cooling means 90 in which the biomass treated liquid at a high temperature 101A, which has been discharged from the hydrothermal decomposition apparatus 50 in FIG. 7, is cooled; an enzymatic saccharification tank 103 in which a cooled treated liquid 101B is subject to saccharification with an enzyme; a solid-liquid separation apparatus 112 in which the water-slightly soluble fermentation inhibitory substances contained in saccharide solution 104, which has been taken out from the enzymatic saccharification tank 103, are removed and a foreign substance removing unit 113 provided with a microfiltration (MF) membrane 113a; a dilution tank 132 which is disposed downstream of the foreign substance removing unit 113 and in which the saccharide solution 104 from which the water-slightly soluble fermentation inhibitory substances has been removed is diluted by adding water thereto; a water separation unit 116 provided with a reverse osmosis (RO) membrane 116a capable of removing water 114 from the diluted saccharide solution 104 to obtain concentrated saccharide solution 115; and a fermentation tank 141 in which the concentrated saccharide solution 115 is subjected to fermentation.

Yeast 142 is added to the fermentation tank 141, thereby obtaining fermentation liquid 143. The fermentation liquid 143 is separately subjected to distillation treatment to obtain a desired fermentation product.

According to the present Example, a solid-liquid separation apparatus 112 is disposed as an apparatus for removing the water-slightly soluble fermentation inhibitory substances which are contained in the saccharide solution 104 taken out from the enzymatic saccharification tank 103, and a foreign substance removing unit 113 provided with a microfiltlation microfiltration (MF) membrane 113a is further disposed downstream thereof.

When the apparatus for removing the water-slightly soluble fermentation inhibitory substance is disposed, the water-slightly soluble fermentation inhibitory substances are removed from the biomass treated liquid at a high temperature generated by decomposing the biomass feedstock in conditions of a high temperature and a high pressure, whereby the saccharide solution including less impurities can be obtained, thus resulting in performance of good fermentation.

Here, it has been confirmed by the present inventors that the water-slightly soluble fermentation inhibitory substances in the present invention are substances different from furfural and HMF (5-hydroxymethyl furfural), which are generally known as fermentation inhibitory substances, though further details about such substances have not been unraveled yet, as explained in Experiment Examples described below.

For example, according to a known hydrothermal decomposition treatment, the biomass and the pressurized hot water are supplied so that they are brought into countercurrent contact with each other, thereby performing the hydrothermal reaction due to the internal heat exchange, as described above. At that time, the reaction condition is that a temperature is high such that the internal temperature is from 180° C. to 240° C. and, at the same time, a pressure 0.1 to 0.4 MPa higher than the saturated steam pressure of water having a temperature at that time is applied, and thus reaction decomposition products of lignin and the like are included in the biomass treated liquid at a high temperature (pressurized hot water effluent) after the reaction.

The pressurized hot water soluble component dissolved in this biomass treated liquid at a high temperature is cooled to an enzymatic saccharification temperature (for example, 60° C. or lower), in a saccharification step of a subsequent step, and thus a part of the pressurized hot water soluble component, which has been once dissolved in pressurized hot water, is precipitated, and is solidified or is formed into a colloidal water-slightly soluble substance.

When the biomass feedstock is subjected to a decomposition treatment at an ordinary temperature, accordingly, these water-slightly soluble substances do not exist on the liquid side, and thus it can be assumed that the water-slightly soluble substances are unique substances in the biomass treated liquid at a high temperature.

According to the present invention, such water-slightly soluble fermentation inhibitory substances are removed by means of a saccharide solution purification means 110, whereby the purification is performed in the saccharification treatment, and thus in a subsequent fermentation step it is possible to perform good fermentation treatment and to improve a fermentation efficiency in an alcohol fermentation, as explained in Experiment Examples described above.

Here, the saccharide solution purification means 110 includes, as illustrated in FIG. 1, the solid-liquid separation apparatus 112 in which solid residue 111 such as lignin including the water-slightly soluble fermentation inhibitory substances 111 is separated from the saccharide solution 104 taken out from the enzymatic saccharification tank 103, and the foreign substance removing unit 113 provided with the microfiltlation (MF) membrane 113a in which the remaining water-slightly soluble fermentation inhibitory substance is further removed from the saccharide solution 104, which has been separated in the solid-liquid separation apparatus 112.

As the solid-liquid separation apparatus 112, for example, a screw decanter, a sand separator, an MF membrane, and the like may be used. The solid substances are removed by using this to protect the RO membrane 116a.

The alcohol fermentation apparatus 200A that uses biomass as a feedstock according to the present Example include the dilution tank 132 in which water (RO water) 131 was added to the saccharide solution 104 from which the water-slightly soluble fermentation inhibitory substances have been removed to dilute it. In FIG. 1, reference sign $P_6$ shows a liquid sending pump for sending dilution water 133 to the water separation unit 116.

When addition of water before the solid substances are removed, only the water-slightly soluble fermentation inhibitory substance in an amount of its solubility is dissolved, and thus a concentration of the fermentation inhibitory substance is not reduced. When the dilution with water is performed after the water-slightly soluble fermentation inhibitory substances are removed, however, it is possible to remove organic acids (for example, acetic acid) and the like other than the decomposition products such as lignin, and to perform the fermentation with high efficiency in the subsequent steps.

Water 114 was removed from the dilution water 133, which has been diluted in the dilution tank 132, through the water separation unit 116 having the RO (Reverse Osmosis: RO) membrane 116a to concentrate it to a pre-determined concentration, thereby obtaining concentrated saccharide solution 115.

Subsequently, the concentrated saccharide solution 115 is sent to the fermentation tank 141, to which yeast 142 is added to obtain the fermentation liquid 143.

In the water separation unit 116, a loose RO membrane, a nanofiltration membrane (NF membrane), and the like may be used.

In the present Example, in order to remove the solid residue 111 such as lignin including the water-slightly soluble fermentation inhibitory substance, the solid-liquid separation treatment in the solid-liquid separation apparatus 112 and the membrane treatment in the foreign substance removing unit 113 are preformed, whereby the fermentation inhibitory substances can be effectively removed.

In particular, many zymocytes capable of fermenting saccharide solution (C5 saccharide), which is obtained by subjecting the hemicellulose, which is the pressurized hot water soluble component, to the saccharification, have poor ethanol resistance and poor resistance to fermentation inhibitory substances, and thus it is important to fit to the resistances of the zymocyte. The present invention can realize it. In fermentation in which a recombinant yeast cannot be used, the resistance of the zymocyte remarkably becomes problems, but the problems can be solved by the present invention.

The decomposition products of the water-slightly soluble fermentation inhibitory substance including lignin are removed during the treatment of the saccharide solution 104, and thus the precipitation of the foreign substances on the RO membrane 116a, which is disposed downstream and is used for separating water, can be prevented, whereby the membrane life of the RO membrane 116a can be prolonged.

Next, the treatment procedure of the alcohol fermentation apparatus 200A using this biomass will be explained.

As the pressurized hot water effluent in the present invention mainly includes the hemicellulose component, the saccharide solution is purified when C5 saccharide and membrane treatment is performed, in which this pressurized hot water soluble component is subjected to enzymatic saccharification to form pentose (C5 saccharide).

<Enzymatic Saccharification Step>

First, the biomass treated liquid at a high temperature (pressurized hot water effluent) 101A is introduced into the enzymatic saccharification tank 103, to which enzyme 102 is added, and the saccharification is performed by the enzyme reaction in the enzymatic saccharification step.

<Solid-Liquid Separation Step>

Next, the saccharide solution 104 is retained in a first saccharide solution tank 121. After that, the solid residue 111 such as lignin including the water-slightly soluble fermentation inhibitory substances is separated through the solid-liquid separation apparatus 112, and then the saccharide solution 104 is retained in a second saccharide solution tank 122.

<Foreign Substance Removing Step>

Next, remaining foreign substances, such as solid residue 111 such as lignin including the water-slightly soluble fermentation inhibitory substances, are membrane-separated from the saccharide solution 104 through the foreign substance removing unit 113 provided with the MF membrane 113a, and then the saccharide solution 104 is retained in the dilution tank 132.

The saccharide solution 104 including the foreign substances, which have not been removed, is returned to the first saccharide solution tank 121 or the second saccharide solution tank 122.

<Saccharide solution Dilution Step>

Next, water (RO water) 131 is added to the saccharide solution 104, from which the water-slightly soluble fermentation inhibitory substances have been removed, in the dilution tank 132 to obtain the dilution water 133.

<Saccharide Concentration Step>

Next, water 114 is removed from the dilution water 133 through the water separation unit 116 provided with the RO membrane 116a to obtain the concentrated saccharide solution 115.

A first measuring unit of measuring either or both of a turbidity and an absorbance of the concentrated saccharide solution 115, which has been purified through the saccharide solution purification means 110 and from which the water-slightly soluble substances have been removed, (for example, a turbidimeter and/or a absorption spectrometer) may be included.

In order to monitor a degree of the impurity removal in the concentrated saccharide solution 115 (a degree of clarity of the saccharide solution 104), the turbidity and/or the absorbance are/is measured in the first measurement unit.

As a result, it is possible to confirm the sufficient removal of the water-slightly soluble substances from the concentrated saccharide solution 115, whereby the quality of the saccharide solution 104 can be controlled by the turbidimeter and/or the absorption spectrometer based on the degree of clarity.

In addition, because it is comprehended that the saccharide solution 104 is sufficiently clear in the first measurement unit, the process control of the ethanol production in the fermentation step can be performed in the second measurement unit by change in the degree of clarity, i.e. the increase or decrease of the degree of clarity, caused by proliferation of yeast 142 in the subsequent step.

<Fermentation Step>

Next, the concentrated saccharide solution is purified in the saccharide solution purification means 110, and is introduced into a fermentation tank 141, and yeast 142 is added thereto, whereby, for example, alcohol fermentation in the fermentation step is performed.

In FIG. 1, reference signs $M_1$ to $M_3$ show motors which drive the stirring means in the enzymatic saccharification tank 103 and the first and second saccharide solution tanks 121 and 122, $M_5$ shows a motor which drives the stirring means by which the stirring is performed in the fermentation tank 141, $P_1$ to $P_3$ show liquid sending pumps for sending the saccharide solution 104, and $P_5$ shows a liquid sending pump for sending the ethanol fermentation liquid 143.

As described above, according to the present Example, the saccharide solution having less impurities can be obtained by removing the water-slightly soluble fermentation inhibitory substances, which are included in the biomass treated liquid at a high temperature 101A generated by decomposition of the biomass feedstock in conditions of a high temperature and a high pressure through the saccharide solution purification means 110, and the fermentation inhibition can be suppressed in the fermentation treatment in the subsequent alcohol fermentation step, thus resulting in performance of good fermentation.

Example 2

Next, a fermentation apparatus that uses biomass as a feedstock will be explained in reference to a view.

Figure 2:
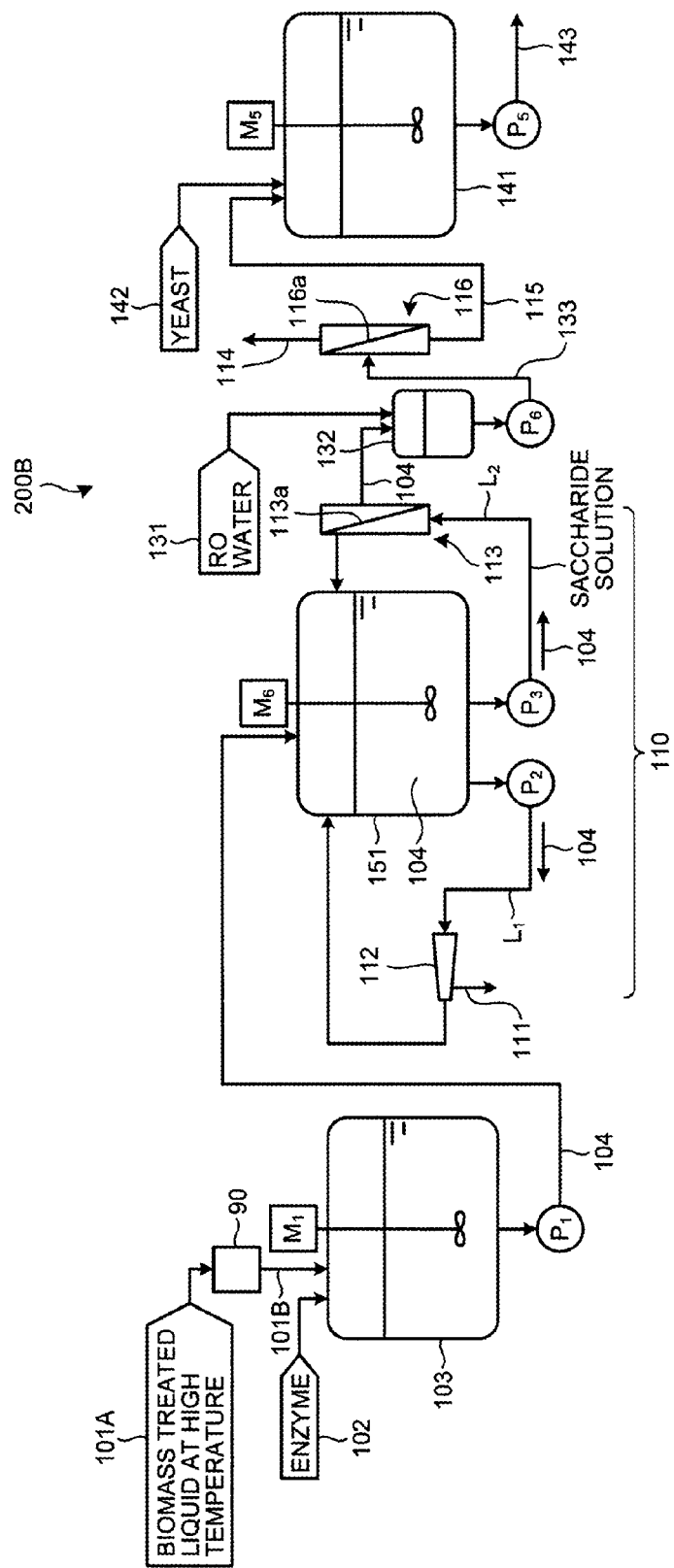
FIG. 2 is a schematic view of a fermentation apparatus that uses biomass as a feedstock according to Example 2.

FIG. 2 is the schematic view of the fermentation apparatus that uses biomass as a feedstock according to Example 2. The same reference signs are applied to the same members as those in the apparatus of Example 1, and the explanations thereof are omitted.

As illustrated in FIG. 2, a saccharide solution purification means 110 having a structure different from that in Example 1 illustrated in FIG. 1 is disposed in a fermentation apparatus 200B that uses biomass as a feedstock.

The saccharide solution purification means 110 illustrated in FIG. 2 includes a saccharide solution purification tank 151 in which saccharide solution 104 taken out from an enzymatic saccharification tank 103 is retained; a solid-liquid separation apparatus (for example, centrifugation) 112 which is disposed via a first circulation line $L_1$ from the saccharide solution purification tank 151, and in which water-slightly soluble fermentation inhibitory substances (solid residue 111 such as lignin) is removed from the taken saccharide solution 104; and a foreign substance removing unit 113 which is disposed via a second circulation line $L_2$ from the saccharide solution purification tank 151, and which includes a microfiltration (MF) membrane 113a removing water-slightly soluble fermentation inhibitory substances from the taken saccharide solution 104.

In FIG. 2, reference sign $M_6$ shows a motor which drives a stirring means in the saccharide solution purification tank 151.

According to the saccharide solution purification means 110 of Example 1, the membrane treatment is sequentially performed, but according to the saccharide solution purification means 110 of Example 2 the saccharide solution purification tank 151 has two circulation lines (the first circulation line $L_1$ and the second circulation line $L_2$), and thus the treatment appropriate to the concentration condition of the water-slightly soluble fermentation inhibitory substance (solid residue 111 such as lignin) can be performed.

When a content of the water-slightly soluble fermentation inhibitory substance (solid residue such as lignin) is higher than a pre-determined value, accordingly, the treatment using both of the first circulation line $L_1$ and the second circulation line $L_2$ is performed to remove the water-slightly soluble fermentation inhibitory substances.

When the content of the water-slightly soluble fermentation inhibitory substance is low, the membrane treatment using the second circulation line $L_2$ alone can be performed. If necessary, the solid-liquid separation treatment may be performed.

Example 3

Next, the fermentation apparatus that uses biomass as a feedstock according to the present invention will be explained in reference to a view.

Figure 3:
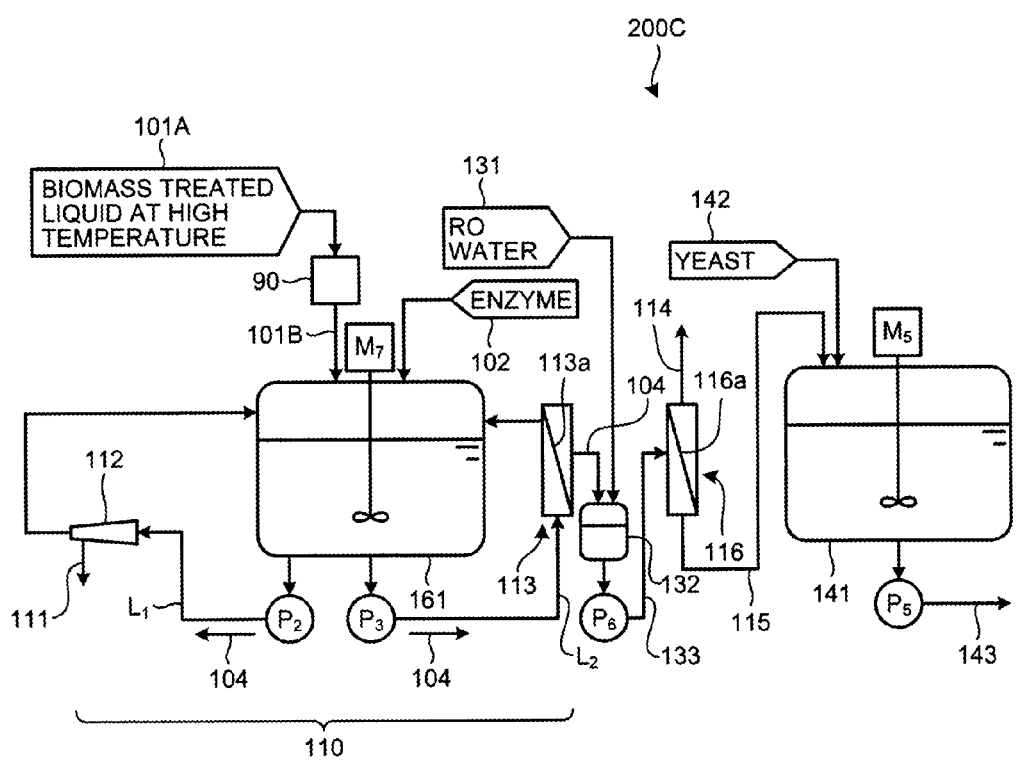
FIG. 3 is a schematic view of a fermentation apparatus that uses biomass as a feedstock according to Example 3.

FIG. 3 is a schematic view of a fermentation apparatus that uses biomass as a feedstock according to Example 3. The same reference signs are applied to the same members as those in the apparatuses of Examples 1 and 2, and the explanations thereof are omitted.

As illustrated in FIG. 3, an alcohol fermentation apparatus 200C that uses biomass as a feedstock includes a saccharide solution purification tank 161 in which the enzymatic saccharification tank 103 in the saccharide solution purification means 110 of Example 2 and the saccharide solution purification tank 151 are integrated.

In the view, reference sign $M_7$ shows a motor which drives a stirring means in the saccharide solution purification tank 161.

According to Example 2, the enzymatic saccharification tank 103 and the saccharide solution purification tank 151 are separately disposed, but according to the present Example, installation space-saving can be contemplated by integrating them.

Experiment Example 1

<Identification Test of Water-Slightly Soluble Fermentation Inhibitory Substance>

Cooled biomass treated liquid at a high temperature and each of various solvents were mixed in a ratio of 1:9, and the identification was performed using a high-performance liquid chromatography apparatus.

The biomass treated liquid at a high temperature was obtained by hydrothermally decomposing rice straw in a pressurized condition having a temperature of 180° C. using a hydrothermal decomposition apparatus 50 illustrated in FIG. 7, and a pressurized hot water effluent 101A was used.

Acetonitrile, acetone, and methanol, which are all polar solvents, were used as a solvent. Pure water, which had been filtered through "MILLI-Q" (trademark), was used as Comparative Example.

The procedures are as follows: the cooled biomass treated liquid at a high temperature was mixed with these solvents and water, and the mixtures were allowed to stand in a refrigerator (4° C.) over night.

After that, centrifugal separation (15,000 rpm, 10 minutes, 4° C.) was performed, and supernatant liquid was recovered and the liquid was treated with a filter (0.45 μm).

This test liquid (Test 1-1: acetonitrile, Test 1-2: acetone, Test 1-3: methanol, and Test 1-4: pure water), after treated with the filter was analyzed using high-performance liquid chromatography (HPLC).

ODS column (SYNERGI: 4μ, Hydro-RP80A 4.6×250 mm, manufactured by Phenomenex Company) was used as the column.

Water-acetonitrile solvent was used as eluent, which was subjected to a gradient treatment of an acetonitrile concentration of 8% to 100%.

A detection wavelength was set at 220 nm.

Figure 4:
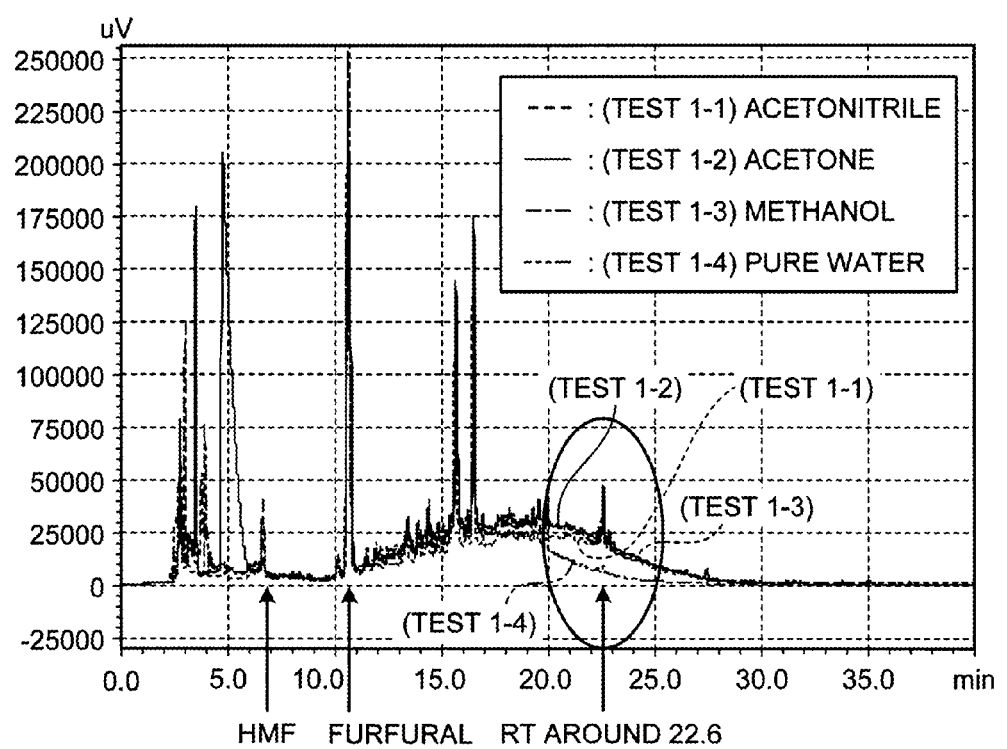
FIG. 4 is a measured chart of a high-performance liquid chromatography.

The results are shown in FIG. 4 and Table 1.

TABLE 1

|  | Furfural | Unknown peak (RT: 22.6 min, Acetonitrile 55%) |
|---|---|---|
| (1-1) Acetonitrile | 2469009 | 160550 |
| (1-2) Acetone | 2513992 | 157743 |
| (1-3) Methanol | 2428062 | 145366 |
| (1-4) Pure water | 2433687 | 22275 |

FIG. 4 illustrates a measured chart of high-performance liquid chromatography.

As shown in FIG. 4 and Table 1, HMF (5-hydroxymethyl furfural: an elution time of around 6.5 minutes) and furfural (an elution time of around 10.5 minutes), which are known fermentation inhibitory substances, were detected in All of Tests 1-1 to 1-4.

On the other hand, an unknown component was identified at an elution time of around 22.6 minutes in Tests 1-1 to 1-3. In Test 1-4, the unknown peak component was not detected.

From the above, it was proved that the biomass treated liquid at a high temperature was contained with a water-slightly soluble substance.

Experiment Example 2

<Fermentation Test According to Presence or Absence of Water-Slightly Soluble Fermentation Inhibitory Substance>

Fermentation of the saccharification liquid using the cooled biomass treated liquid at a high temperature was performed, and $CO_2$ decreased amounts in the fermentation were compared.

*Pichia stipitis* NBRC1687 (standard stock) was used as strain.

A pre-culture condition was that 10 mL YPD (1% yeast extract, 2% peptone, 2% glucose) was used as a medium, and shaking culture was performed at 30° C. at 120 rpm.

The fermented liquid which had been passed through a filter (0.45 μm), and the fermented liquid which had not been passed through the filter (0.45 μm) were prepared, and the fermentation was performed.

An ethanol fermentation condition was that 100 mL of fermentation liquid was used and shaking culture was performed at 30° C. at 120 rpm.

The fermentation conditions and the test results are shown in Table 2 and Table 3.

TABLE 2

| Test No. | Solvent | Filter (0.45 nm) | Nutrient, Final saccharide concentration | | | |
|---|---|---|---|---|---|---|
| | | | Yeast ex.* (%) | CSL* (%) | Glucose (%) | Xylose (%) |
| (2-1) | Saccharide solution from biomass treated at high temperature (C5 saccharide) | Absent | 0 | 0 | 7.2 | 8.5 |
| (2-2) | | Present | | | | |
| (2-3) | | Absent | 1.0 | 1.0 | | |
| (2-4) | | Present | | | | |

Condition: 100 mL of fermented liquid, 30° C., 120 rpm Shaking culture
*Yeast ex.: Yeast extract
*CSL: Corn steep liquor
Strain used: *Pichia stipitis* NBRC1687 (standard strain)
Pre-culture conditions: Medium 10 mL YPD (1% Yeast ex.*, 2% Peptone, 2% Glucose)
Conditions 30° C., 120 rpm Shaking culture

TABLE 3

Final concentration of Glucose, Xylose, or EtOH Concentration

| Test No. | Glucose (%) | Xylose (%) | EtOH (%) | Fermentation efficiency (%) |
|---|---|---|---|---|
| (2-1) | 5.9 | 7.2 | N.D. | 0 |
| (2-2) | 3.7 | 7.1 | 0.9 | 11 |
| (2-3) | 5.4 | 7.4 | N.D. | 0 |
| (2-4) | N.D. | 5.0 | 3.0 | 38 |

N.D.: Not Detected

Figure 5:
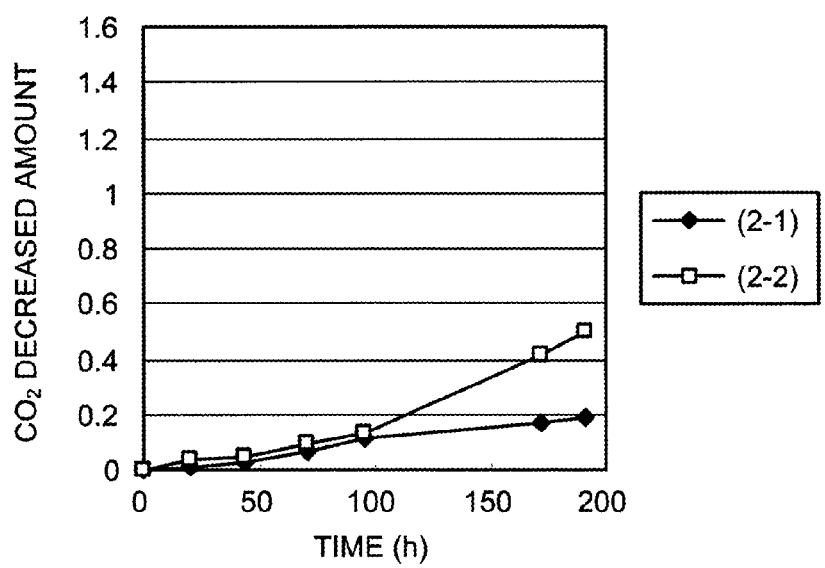
FIG. 5 is a view illustrating results of decreased amounts of carbon dioxide in an ethanol fermentation test.
Figure 6:
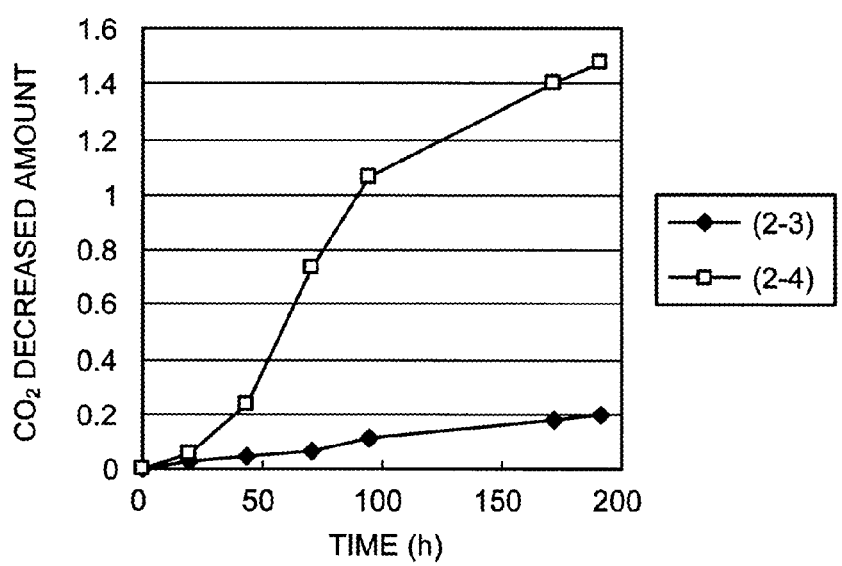
FIG. 6 is a view illustrating results of decreased amount of carbon dioxide in an ethanol fermentation test.

FIG. 5 and FIG. 6 are charts illustrating the results of decreased amounts of carbon dioxide in the ethanol fermentation test, in which the horizontal axis shows time, and the vertical axis shows a $CO_2$ decreased amount.

As illustrated in FIG. 5 and FIG. 6, the fermentation test showed that the difference in the decreased amount of carbon dioxide appeared after about 90 hours passed in Test 2-2 (no nutrient, presence of the filter) compared to Test 2-1 (no nutrient, no filter).

The difference in the decreased amount of carbon dioxide appeared after about 20 hours passed and after that the decreased amount was remarkably increased in Test 2-4 (presence of nutrient, presence of the filter) compared to Test 2-3 (presence of nutrient, no filter).

The fermentation efficiency was 11% in Test 2-2, and the fermentation efficiency was 38% in Test 2-4.

It was confirmed, therefore, that when the treatment with a filter (0.45 μm) was performed, the water-slightly soluble fermentation inhibitory substances are removed, resulting in performance of good fermentation.

As described above, it was proved that when the water-slightly soluble fermentation inhibitory substances were removed by the saccharide solution purification means, the saccharide solution including less impurities could be obtained, and the fermentation inhibition could be remarkably suppressed in the alcohol fermentation treatment in the subsequent steps.

REFERENCE SIGNS LIST 50 hydrothermal decomposition apparatus
51 biomass feedstock
52 biomass supplying unit
53 apparatus body
54 conveying screw means
55 pressurized hot water
56 biomass solid component
57 biomass discharging unit
90 cooling means
101A biomass treated liquid at a high temperature (pressurized hot water effluent)
101B cooled treated liquid
102 enzyme
103 enzymatic saccharification tank
104 saccharide solution
110 saccharide solution purification means
141: fermentation tank
142 yeast
200A to 200C alcohol fermentation apparatus that uses biomass as a feedstock

The invention claimed is:

1. A fermentation apparatus that uses biomass as a feedstock comprising:
   a hydrothermal decomposition apparatus that brings a biomass feedstock including at least cellulose, hemicellulose, and lignin into countercurrent contact with pressurized hot water and performs a high temperature and high pressure treatment in a temperature range of 180° C. to 240° C. so as to produce a biomass treated liquid containing a pressurized hot water soluble component of the biomass feedstock;
   a cooling means that is provided downstream of the hydrothermal decomposition apparatus and cools the biomass treated liquid which has been discharged from the hydrothermal decomposition apparatus;
   a saccharide solution purification tank that is provided downstream of the cooling means and saccharifies the cooled treated liquid with an enzyme so as to obtain a saccharide solution;
   a first circulation line that connects between a bottom portion of the saccharide solution purification tank and an upper portion of the saccharide solution purification tank to circulate the saccharide solution;
   a second circulation line that connects between the bottom portion of the saccharide solution purification tank and the upper portion of the saccharide solution purification tank to circulate the saccharide solution;
   a solid-liquid separation apparatus that is interposed in the first circulation line and removes a fermentation inhibitory substance contained in the saccharide solution, the fermentation inhibitory substance being a substance that is contained in the pressurized hot water soluble component, and that is in a liquid state in the temperature range of 180° C. to 240° C. and becomes solidified or colloidal at a temperature of 60° C. or lower;
   a foreign substance removing unit that is interposed in the second circulation line and further provided with a microfiltration (MF) membrane by which the fermentation inhibitory substance is further removed;
   a dilution tank that is disposed downstream of the foreign substance removing unit and adds water thereto so as to dilute the saccharide solution from which the fermentation inhibitory substance has been removed;
   a water separation unit that is provided with a reverse osmosis (RO) membrane and removes water from the diluted saccharide solution so as to obtain concentrated saccharide solution;
   a fermentation tank that ferments the concentrated saccharide solution; and
   a first measurement unit that measures either or both of a turbidity or/and a light absorbance of the saccharide solution from which the fermentation inhibitory substance has been removed.

2. The apparatus according to claim 1, further comprising a second measurement unit that measures either or both of a turbidity and a light absorbance of the saccharide solution after addition of yeast.

* * * * *